US010026167B1

United States Patent
Hofmann et al.

(10) Patent No.: US 10,026,167 B1
(45) Date of Patent: Jul. 17, 2018

(54) METHOD OF OBTAINING MICROGRAPHS OF TRANSPARENT OR SEMI-TRANSPARENT SPECIMENS USING ANISOTROPIC CONTRAST

(71) Applicants: J. A. WOOLLAM CO., INC., Lincoln, NE (US); BOARD OF REGENTS OF THE UNIVERSITY OF NEBRASKA, Lincoln, NE (US)

(72) Inventors: Tino Hofmann, Lincoln, NE (US); Mathias M. Schubert, Lincoln, NE (US); Tadas Kasputis, Canton, MI (US); Angela K. Pannier, Lincoln, NE (US); Craig M. Herzinger, Lincoln, NE (US); John A. Woollam, Lincoln, NE (US)

(73) Assignees: BOARD OF REGENTS OF THE UNIVERSITY OF NEBRASKA, Lincoln, NE (US), part interest; J. A. WOOLLAM CO., INC., Lincoln, NE (US), part interest ( * ) Notice: Subject to any disclaimer, the term of this patent is extended or adjusted under 35 U.S.C. 154(b) by 292 days.

(21) Appl. No.: 14/757,232

(22) Filed: Dec. 9, 2015

Related U.S. Application Data

(60) Provisional application No. 62/124,195, filed on Dec. 11, 2014.

(51) Int. Cl.
  *G06T 7/00* (2017.01)
  *G01J 4/00* (2006.01)
  *G01N 21/23* (2006.01)
  *G01N 21/21* (2006.01)
  *G06K 9/46* (2006.01)
  *G01J 4/04* (2006.01)

(52) U.S. Cl.
  CPC .............. *G06T 7/0012* (2013.01); *G01J 4/00* (2013.01); *G01J 4/04* (2013.01); *G01N 21/21* (2013.01); *G01N 21/23* (2013.01); *G06K 9/46* (2013.01); *G01J 2004/001* (2013.01); *G06T 2207/10012* (2013.01); *G06T 2207/10056* (2013.01); *G06T 2207/30024* (2013.01)

(58) Field of Classification Search
  CPC ... G01B 11/06; G01B 11/0641; G01B 11/065; G01N 21/19; G01N 21/21; G01N 21/211; G01N 21/23; G01N 21/41; G01J 4/00; G01J 4/02; G01J 4/04; G01J 2004/001; G01J 2004/002; G01J 2004/004; G01J 2004/005; G01J 2004/007; G01J 2004/008; G06T 7/0012; G06T 2207/10056; G06T 2207/10012; G06T 2207/30024; G06K 9/46
  See application file for complete search history.

(56) References Cited

U.S. PATENT DOCUMENTS

| 7,889,339 | B1 * | 2/2011 | Flock | G01N 21/211 356/364 |
| 2003/0117624 | A1 * | 6/2003 | Daniels | G01J 4/04 356/364 |

(Continued)

*Primary Examiner* — Gordon J Stock, Jr.
(74) *Attorney, Agent, or Firm* — James D. Welch

(57) ABSTRACT

Anisotropic contrast methodology in combination with use of sample investigating polarized electromagnetic radiation to provide Jones or Mueller Matrix imaging data corresponding to areas on samples.

38 Claims, 8 Drawing Sheets

(56) References Cited

U.S. PATENT DOCUMENTS

2014/0106980 A1* 4/2014 Schubert ............... G01N 21/23
 506/9
2016/0116397 A1* 4/2016 Freudenthal ........... G01N 21/23
 356/370

* cited by examiner

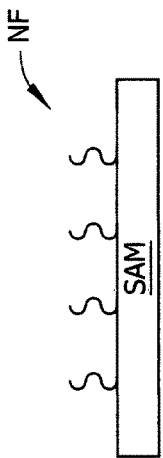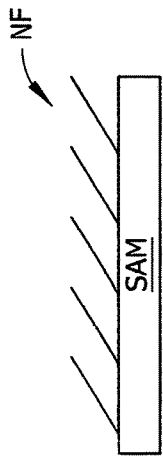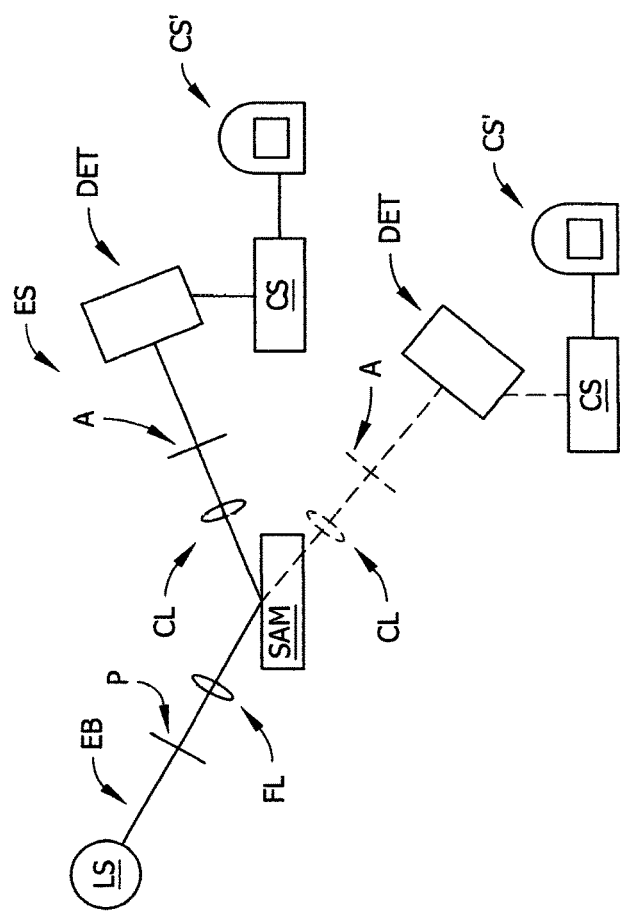

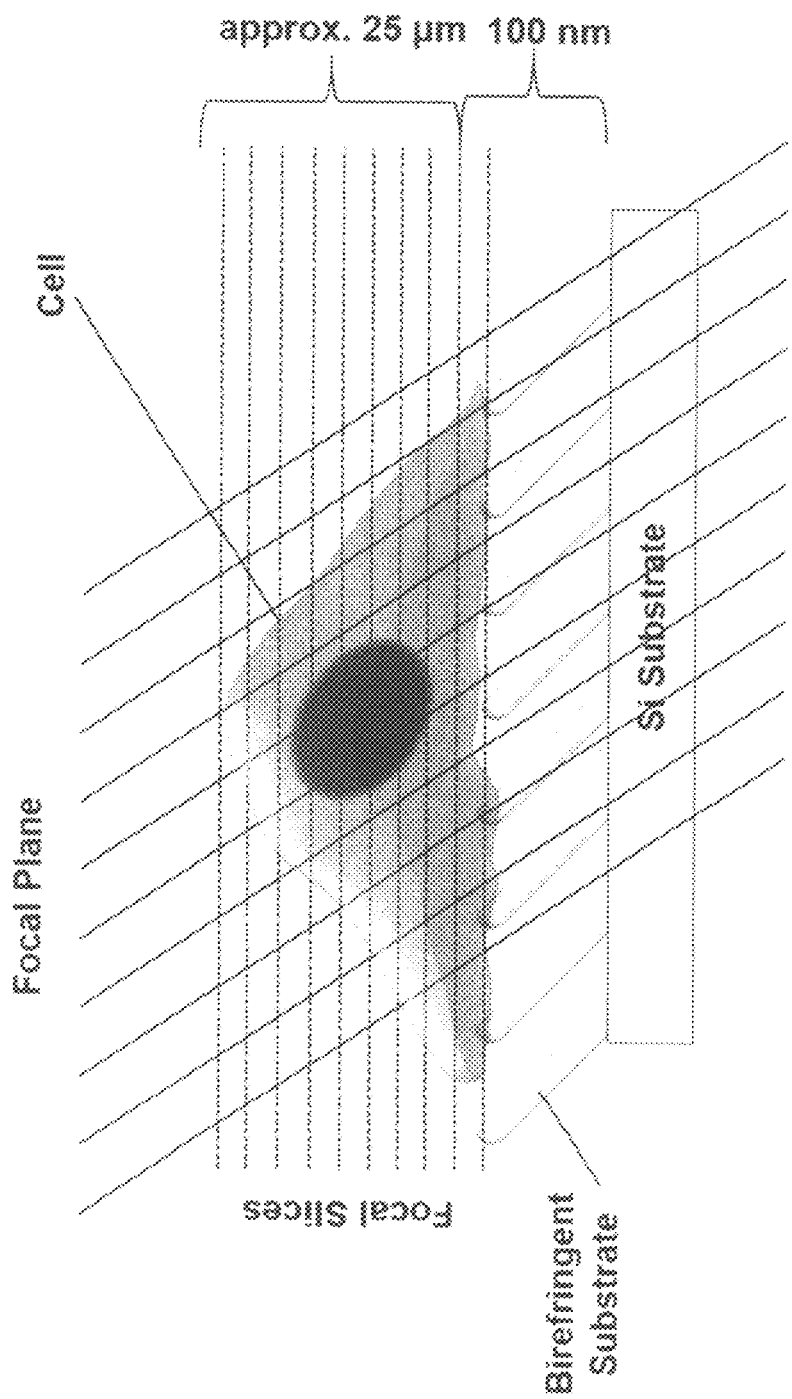

METHOD OF OBTAINING MICROGRAPHS OF TRANSPARENT OR SEMI-TRANSPARENT SPECIMENS USING ANISOTROPIC CONTRAST

This Application Claims benefit of Provisional Application Ser. No. 62/124,195 Filed Dec. 11, 2014.

TECHNICAL FIELD

The present invention relates to non-destructive methods for producing magnified images of samples, and more particularly to methodology that does not require fluorescent labeling or lapping and staining or contrast media or fixing procedures of any kind, but instead applies an anisotropic contrast technique in combination with use of sample investigating polarized electromagnetic radiation to provide Jones or Mueller Matrix imaging data corresponding to areas on samples.

BACKGROUND

Nanostructured topologies have the potential to endow biomedical materials with functions that can direct cell behaviors and facilitate biomolecule retention and release. However, the design of such materials is limited due to a lack of mechanistic understanding of how biomolecules interact with nanostructured substrates. Further, current approaches to imaging techniques are often destructive, in that cells must be modified by means of cell fixing and labeling, to obtain images of specific cell organelles, proteins or nucleic acids. Furthermore, currently available imaging modalities are not able to provide images of cells' interactions with their local microenvironment, such as infiltrations with two and three dimensional substrates. Additionally, for cell interactions with nanostructure materials, which is of particular interest as regards the present invention, real-time observations of cellular infiltration into nanostructures, forces exhibited by cells as they migrate, and cellular remodeling of a microenvironment (eg. by secreting proteins) remain challenging.

Continuing, Ellipsometry is a widely used optical technique for characterization of organic thin films. Ellipsometry involves directing polarized electromagnetic radiation at a sample, and monitoring change in said polarization state based on interaction, (eg. reflection or transmission), therewith. Said change in polarization can be converted to meaningful output, such as film thickness and mass density for instance. While traditional ellipsometric techniques commonly average change in polarization state over an area of a sample, imaging ellipsometry (IE), (ie. a combination of ellipsometry and optical microscopy), enables spatial resolution of said polarization state changes on a per pixel basis.

It is noted at this point that the while investigating cell behaviors which, for instance, facilitate biomolecule retention and release and the like by imaging techniques is known, there remains need for improved techniques that apply nanostructured materials. The present invention provides such improved techniques by combining imaging ellipsometric polarization contrast microscopy with use of birefringence materials to provide a technique termed Mueller (Jones) Matrix birefringence microscopy (MMBM) to characterize cellular and biomolecular interactions with said nanostructured materials.

A computer Search for Patents and Published Applications that include the terms "anisotropic ellipsometry or birefringent ellipsometry and microscope", returned no hits.

DISCLOSURE OF THE INVENTION

The present invention is a non-destructive method for producing magnified images of samples, which method does not require fluorescent labeling or lapping and staining or contrast media or fixing procedures of any kind, but instead uses an anisotropic contrast technique in combination with use of sample investigating polarized electromagnetic radiation to provide functionally similar information. Said method comprises;

a1) providing an optical system which produces magnified images of samples by an approach involving applying an investigating beam of electromagnetic radiation that has a polarization state imposed thereupon, thereto; and a2) providing at least one anisotropic transparent or semi-transparent element within the beam of electromagnetic radiation pathway.

Said method further comprises:

b) providing a sample and causing it to interact with said at least one anisotropic transparent or semi-transparent element while said beam of electromagnetic radiation is caused to interact therewith;

c) detecting images of electromagnetic radiation reflected from or transmitted through said sample, as a function of the change in polarization state of said beam of electromagnetic radiation caused by interaction with said sample and at least said anisotropic transparent or semi-transparent element;

d) processing data pertaining to said detected images to provide at least some Jones or Mueller Matrix elements including at least one off-diagonal element thereof, that pertain to known "X" "Y" and "Z" locations of said sample;

e) storing and/or displaying said processed data.

Said method can further comprise analyzing detected image data to determine characterizing physical and/or chemical parameters of said sample.

Said method can involve that the investigating beam of electromagnetic radiation is of a desired selectable wavelength in at least the THZ to VUV range and in which data is acquired at a selection from the group consisting of:

a single wavelength; and multiple wavelengths.

Said method can provide that detected images of electromagnetic radiation reflected from or transmitted through said sample involves a light collecting system.

Said method can comprise system capability to vary the position of said sample in "X" "Y" and "Z" directions.

Said method can comprises system capability to vary the location on a sample from which light is collected, in three dimensions.

Said method can comprises system capability that enables varying the sample magnification.

Said method can provide that the system capability that enables varying the sample magnification is achieved by varying the beam path configuration.

Said method can provide that the system further comprises an environmental chamber in which said sample is present.

Said method can provide that the system environmental chamber in which said sample is present is a fluid cell.

Said method can provide that the system comprises a selection from the group consisting of:

one anisotropic transparent or semi-transparent region in an element within the beam of electromagnetic radiation pathway; and more than one anisotropic transparent or semi-transparent region in an element within the beam of electromagnetic radiation pathway;

which element is in proximity to the sample, which one or more anisotropic transparent or semi-transparent element(s) provide contrast in an image of said sample which is coupled therewith, based in changes of beam polarization state.

Said one or more anisotropic transparent or semi-transparent element(s) can demonstrate birefringence and/or dichroism at a selected wavelength at which the optical system forms an image of said sample.

Said one or more anisotropic transparent or semi-transparent element(s) can demonstrate optically uniaxial or optically biaxial properties at a selected wavelength at which the optical system forms an image of said sample, and in which at least one of said optical axes is not oriented perpendicular to the surface of said element.

Said one or more anisotropic transparent or semi-transparent element(s) can demonstrate one or two major axes of dichroic activity, and in which at least one of said axes is not oriented perpendicular to the surface of said element.

Said one or more anisotropic transparent or semi-transparent element(s) can demonstrate one or two major axes of dichroic activity as well as birefringence, and in which at least one of said axes is not oriented perpendicular to the surface of said element.

Said one or more anisotropic transparent or semi-transparent element(s) can be comprised of porous material with regular arrangements of patterns and interspacings that have dimensions smaller than a selected wavelength at which an image of said sample is formed.

Said one or more anisotropic transparent or semi-transparent element(s) can be comprised of columnar nanostructured thin films.

Said one or more anisotropic transparent or semi-transparent element(s) can be columnar nanostructured thin films are twisted chiral.

Said one or more anisotropic transparent or semi-transparent element(s) columnar nanostructured thin films can be formed by glancing angle deposition of micro or nano-fiber producing material.

Said one or more anisotropic transparent or semi-transparent element(s) can be comprised of both isotropic and anisotropic regions, and wherein said isotropic regions can serve as a support structure.

Said one or more anisotropic transparent or semi-transparent element(s), can have the anisotropic region comprised of at least one selection form the group consisting of:
  slanted columns;
  zig-zags;
  helices; and/or
  hollow screws;
attached to a glass slide or plastic film or the like.

The system utilized in practice of said methodology can comprise a polarization state generator and polarization state analyzer each comprises a polarizer.

Further said system can further comprise a compensator in at least one of said polarization state generator and polarization state analyzer.

It is noted that practice of the present invention methodology produces an image of a sample which is a function of both wavelength and beam polarization state.

It is also noted that for each pixel in stored or displayed processed data corresponding to produced Jones or Mueller matrix elements, including at least one off-diagonal element thereof, (J12, J21, M13, M14, M23, M24, M31, M32, M41 and M42), calculates, as a function of initial electromagnetic radiation beam polarization state and of the polarization state of said beam after interaction with said sample and at least one anisotropic transparent or semi-transparent element within the beam of electromagnetic radiation pathway, sample image data.

The present invention methodology can further involve collecting data for the case where no sample is present.

In said case a comparison can be made between data collected for specific "X", "Y" and "Z" positions on a sample when a sample is present and when it is not present and results thereof are stored or displayed.

Further, data collected when a sample is not present, can be subtracted from data collected at the same "X", "Y" and "Z" positions when it is present and results thereof stored or displayed.

Data collected for specific "X", "Y" and "Z" positions on a sample when a sample is present, can also be subtracted from data collected at different "X", "Y" and "Z" positions when it is present, and results thereof stored or displayed.

Data collected for specific "X", "Y" and "Z" positions on a sample when a sample is present, can be subtracted from data collected at the same "X", "Y" and "Z" positions when it is still present, but where system components are varied in position, and results thereof stored or displayed.

Additional computation can be performed to evaluate physical and/or chemical properties of said sample.

Another non-destructive method for imaging at least one selection from the group of samples consisting of;
  biomolecules;
  biomaterial interfaces;
  cells;
  cell interactions;
  tissues; and
  tissue regeneration phenomena;
which method does not require fluorescent labeling or lapping and staining or contrast media or fixing procedures of any kind, but instead uses an anisotropic contrast technique in combination with use of sample investigating polarized electromagnetic radiation to provide functionally similar information. Said method comprises;

a) providing a system capable of generating and imaging at least one element of a Jones or Mueller Matrix, said system comprising:
  a source of electromagnetic radiation;
  a polarization state generator;
  a stage for supporting samples, said stage comprising highly-ordered and micro to nano-scale structure architectures such that when a sample is placed thereupon and investigated with electromagnetic radiation, and an image is generated for said at least one element of a Jones or Mueller matrix, image information is shifted into off-diagonal elements thereof as a result of stage material anisotropy;
  a polarization state detector;
  a data detector for accepting electromagnetic radiation after it interacts with a sample placed onto said stage;
  a computer system for analyzing data provided by said data detector and producing imaging information for at least one element of a Jones or Mueller matrix; and
  a presentation screen for making Jones or Mueller matrix imaging viewable.

Said method continues with:
  b) placing a sample onto said stage;
  c) causing said source of electromagnetic radiation to direct a beam of electromagnetic radiation so that it passes through said polarization state generator, interacts with said sample and stage upon which it is present, passes through said polarization state analyzer and then enters said data detector;

to the end that sample characterizing data produced by said data detector is analyzed and presented for viewing as imaged Jones or Mueller matrix elements.

The provided system can further comprise a focusing lens on one side of said stage for supporting samples, a collimating lens on the other side of said stage for supporting samples such that magnification of images can be obtained.

Said computer system for analyzing data provided by said data detector and producing imaging information for at least one element of a Jones or Mueller matrix and said presentation screen for making Jones or Mueller matrix imaging viewable can be embodied as a camera.

The electromagnetic beam which interacts with said sample and stage upon which it is present can be configured so that it transmits therethrough.

Alternatively, the electromagnetic beam which interacts with said sample and stage upon which it is present can be configured so that it reflects from said sample.

The stage for supporting samples can be fabricated by glancing angle deposition of nano-fiber producing material onto a substrate.

The present invention is also a system capable of generating and imaging at least one off-diagonal element of a Jones or Mueller Matrix that is representative of a sample, said system comprising:
- a source of electromagnetic radiation;
- a polarization state generator;
- a stage for supporting samples, said stage comprising highly-ordered and micro to nano-scale structure architectures such that when a sample is placed thereupon and investigated with electromagnetic radiation, and an image is generated for said at least one element of a Jones or Mueller matrix, image information is shifted into off-diagonal elements thereof as a result of stage material anisotropy;
- a polarization state detector;
- a data detector for accepting electromagnetic radiation after it interacts with a sample placed onto said stage;
- a computer system for analyzing data provided by said data detector and producing imaging information for at least one element of a Jones or Mueller matrix; and
- a presentation screen for making Jones or Mueller matrix imaging viewable.

The stage for supporting samples can be fabricated by glancing angle deposition of nano-fiber producing material onto a substrate.

The present invention will be better understood by reference to the Detailed Description Section of this Specification, with reference to the Drawings

BRIEF DESCRIPTION OF THE DRAWINGS

FIGS. 1aa and 1ab demonstrate nanofiber configurations on samples.

FIG. 1ac generally shows elements of an ellipsometer.

FIG. 1b demonstrates what is meant by polarization modulated images obtained in "10 focal planes through the Z-axis".

DETAILED DESCRIPTION

In contrast to traditional microscopy techniques where cells are commonly imaged on flat substrates, Mueller Matrix Birefringent Microscopy (MMBM) utilizes nanostructured, optically birefringent surfaces, which enhances image construction via substrate anisotropy, and this uniquely situates the present invention technique for the study of protein and cellular interactions on nanoscale features. In the present invention, birefringent substrates were fabricated by depositing titanium (Ti) Spatially Coherent Thin Films (SCTFs) onto reflexive silicon (Si) substrates. SCTFs are fabricated by Glancing Angle Vapor Deposition (GLAD) performed with oblique angle particle flux relative to the substrate, facilitated by electron beam evaporation. This approach results in highly ordered, highly coherent and controllable architectures ranging in size and shape from nano to micro scales, depending on the vapor flux angle and deposition time length. SCTFs provide enlarged surface areas, and enhanced optical properties with applications in photovoltaics, sensing (chemical, biological, optical and pressure), micro and nano fluidics and nanoelectronics.

Figure 1A:
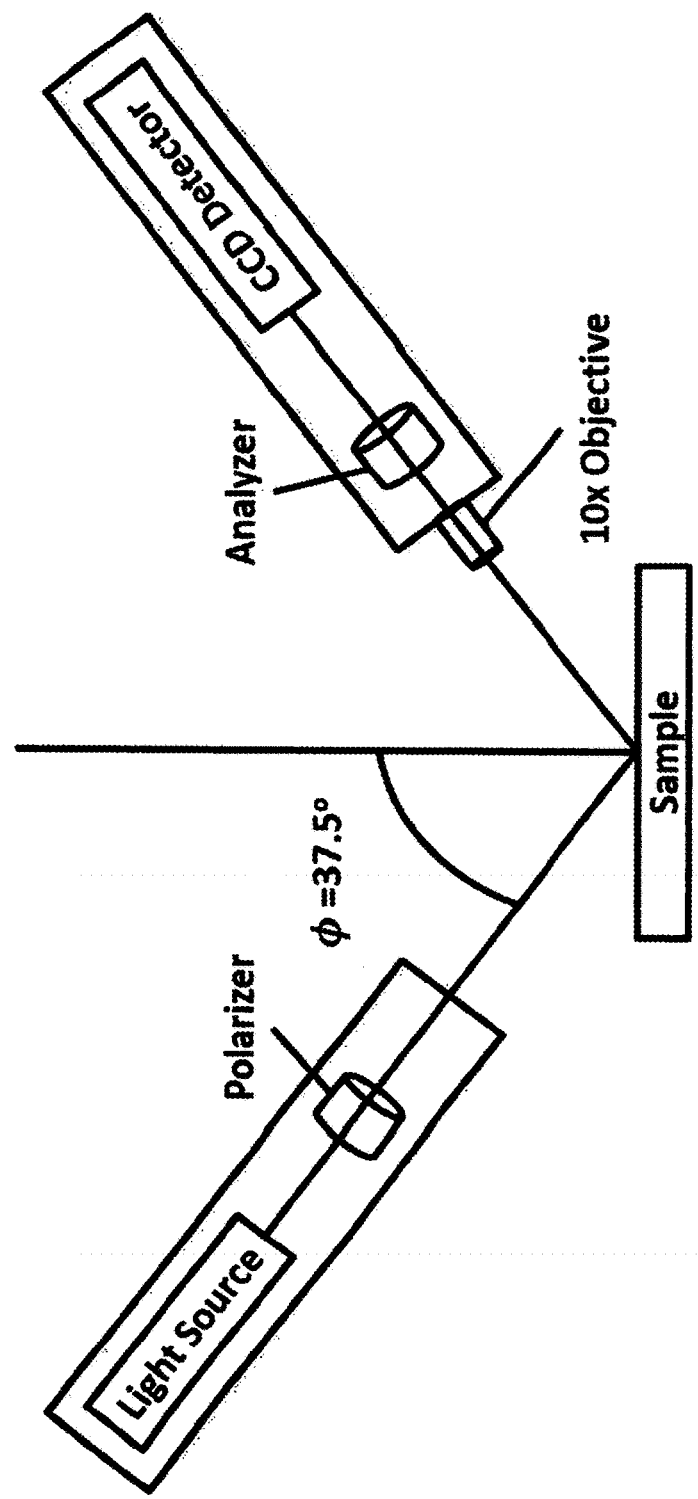
FIG. 1a shows a demonstrative ellipsometer system for investigating samples using present invention methodology.

The present invention realization involved application of Generalized ellipsometry (GE) to characterize the structural parameters prior to use, and a best-fit optical model of the GE spectral data determined that the SCTF film possessed a desired thickness of approximately 100 nm, (actual thickness was 93 nm), with a column slanting angle of 42 degrees with respect to a substrate normal. This indicated a coherently-oriented, anisotropic and birefringent nanostructure surface. A demonstrative ellipsometer system for investigating such is shown in FIG. 1a. FIGS. 1aa and 1ab are included to demonstrate nanofiber (NF) orientations on a sample. FIG. 1aa demonstrates nanofibers (NF) formed by deposition at an angle to a sample (SAM) surface, and FIG. 1ab shows nanofibers (NF) formed by rotating a sample (SAM) during formation thereof. Various structures such as slanted columns; zig-zags; helicies; and/or hollow screws can be utilized.

FIG. 1ac is included to provide general insight to a typical ellipsometer system. Shown are:
- a source of electromagnetic radiation (LS);
- a polarization state generator (P);
- a stage for supporting samples, said stage comprising highly-ordered and micro to nano-scale structure architectures (NF) such that when a sample is placed thereupon and investigated with electromagnetic radiation, and an image is generated for said at least one element of a Jones or Mueller matrix, image information is shifted into off-diagonal elements thereof as a result of stage material anisotropy;
- a polarization state detector (A);
- a data detector for accepting electromagnetic radiation after it interacts with a sample placed onto said stage (DET);
- a computer system (CS) for analyzing data provided by said data detector and producing imaging information for at least one element of a Jones or Mueller matrix; and a presentation screen (CS') for making Jones or Mueller matrix imaging viewable.

Following GLAD fabrication and Generalized Ellipsometry (GE) characterization, the SCTF was sterilized by immersing the sample in 200 proof ethanol, followed by transferring the sample to a 6-well plate in a sterile laminar fluid flow hood to air dry. Then the sample was rinsed twice in IX phosphate buffered saline (PBS), followed by application of 10 microgram/milliliter solution of fibronectin protein (FN) dissolved in PBS to coat the sample with a layer of FN extracellular matrix protein to enhance cell adhesion. After 90 minutes in FN solution, the sample was rinsed again with IX PBS and NIH/3T3 mouse fibroblasts (cultured in Dulbecco's Modified Eagles Media (DMEM)), supplemented with 10% fetal calf serum and 1% penicillin/streptomycin were then seeded at a concentration of 50,000 cells/mL, and cultured in an incubator for 24 hours at 37 degrees Celsius, 5% CO2. On the following day, the sample was transferred to a 10 cm2 Petri dish containing warm media and placed on the stage of the MMBM imaging setup, which primarily consists of commercially available Imaging Ellipsometers (IE).

Figure 2:
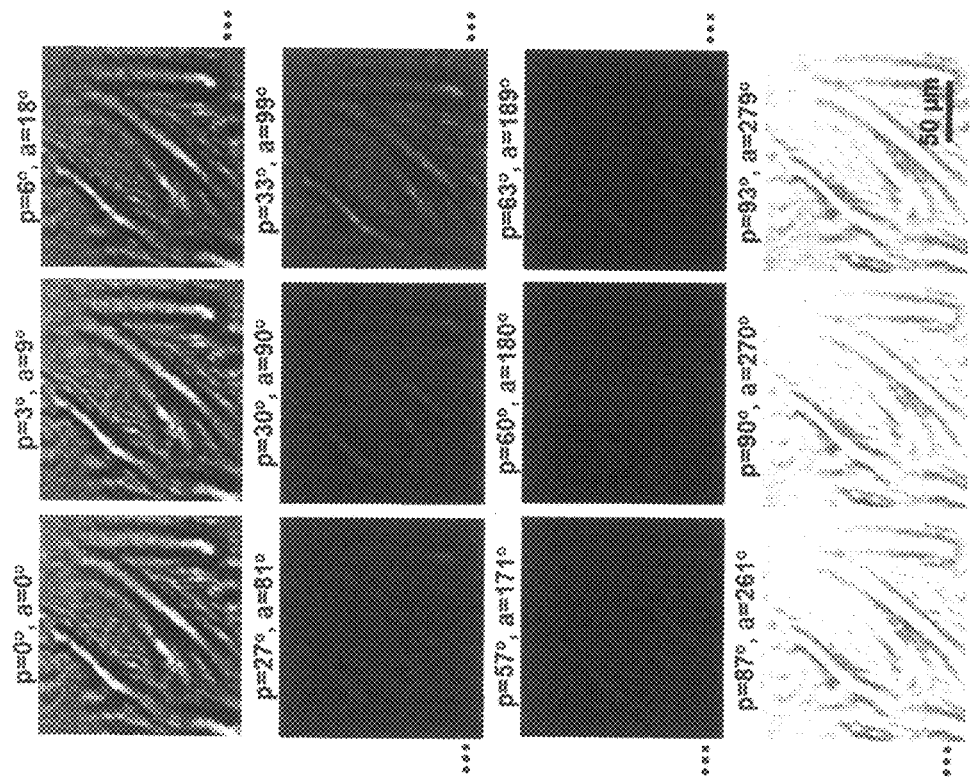
FIG. 2 shows representative polarization contrast images under variation of IE polarization for one focal slice.

An Accurion model EP4 IE was used for all studies and was modified by removing the dual-rotating compensators to achieve a polarizer-analyzer configuration for MMBM imaging. In addition, the imaging ellipsometer utilizes a single-wavelength (685 nm) scanning laser source, a 10× Nikon objective, CCD detector, and was operated in reflection mode with a 37.5 degree angle of incidence. (See FIG. 1A). Measurement of ellipsometric (ie. Mueller Matrix images) was performed in polarization-modulated Fourier analysis based ellipsometry measurements. For the study, polarization modulated images were obtained in 10 focal planes through the Z-axis to obtain of the cell to obtain 10 focal slices of cell images as shown in FIG. 1B. Representative polarization contrast images are shown in FIG. 2 for one focal slice. A total of 120 polarization contrast images were obtained by the MMBM for each of the 10 focal slices. The polarizer (POL) was rotated from 0-180 degrees in increments of 9 degrees, differing by a factor of 3 with respect to the polarizer orientation for each image (see example increments in FIG. 2) Intensity values were obtained for each pixel, and when imaged at a constant exposure rate throughout the study (2500 ms), intensity values change with respect to the changes in polarization. Intensity value per pixel are observed to decrease as the polarization moves from an open parallel-polarization mode (POL=90 degrees) to a cross polarization mode (POL=90 degrees an=270 degrees) to a cross polarization (POL=60 degrees, an=180 degrees). When imaging on flat samples, intensity values in the cross polarization mode yielded negligible values since MMBM is effectively nulling the intensity signal. However, when using birefringent STF's as imaging substrates, the optical anisotropy provided by the nanotopography results in an increase in polarization contrast and dose not result in complete intensity signal nulling as seen in complete intensity signal nulling as seen on the POL=60 degrees, an=180 degrees image.

Figure 3:
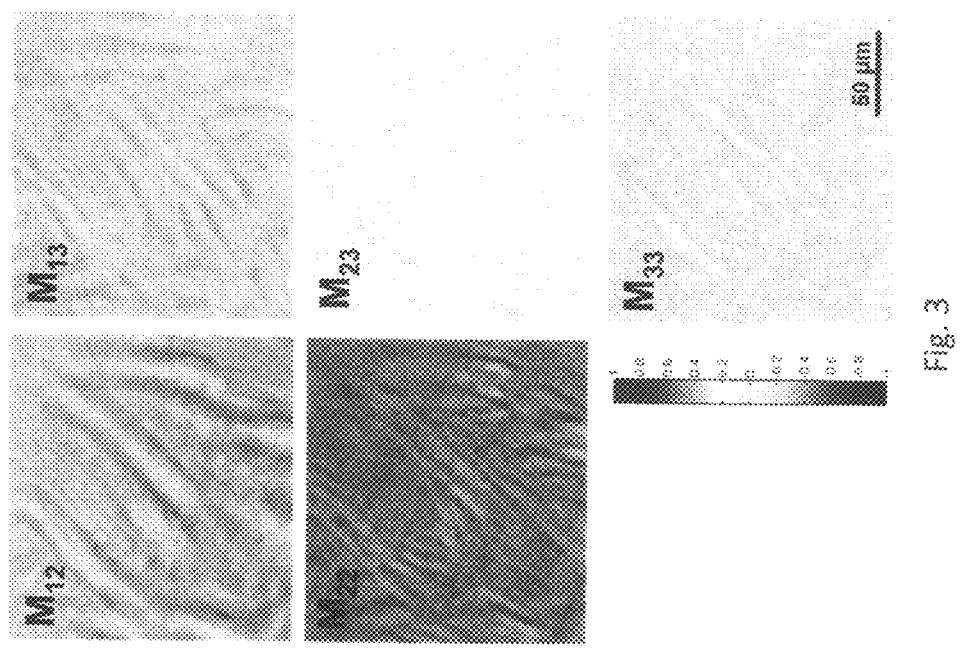
FIG. 3 shows representative polarization contrast images for one focal slice.

The 120 polarization contrast images obtained by the MMBM for each focal length were then processed in MATLAB (Math Works), by applying a geometric Fourier based algorithm to obtain five non-redundant MM elements (M12, M13, M22, M23 and M33) for each focal slice, which contain individual, spatially resolved MM values for each pixel that are normalized to the total intensity (M11) per pixel. (See FIG. 3). This process was repeated for each slice, then each MM element for the individual focal slices was converted to 0-255 greyscale in MATLAB, where a greyscale value of 0 (pure black) is equivalent to an MM reflectance ratio of −1, a greyscale value of 128 (middle grey) is equivalent to MM ratio of 0, and a greyscale of 255 (pure white) is equivalent to a MM ratio of +1. Next, the greyscale MM images were imported into NIH ImageJ64 for further processing to isolate MM values near zero to obtain a MMBM image, with a high degree of contrast, which displays MM values that are correlated to birefringent interactions of the polarized light with cell surface interface.

Figure 4:
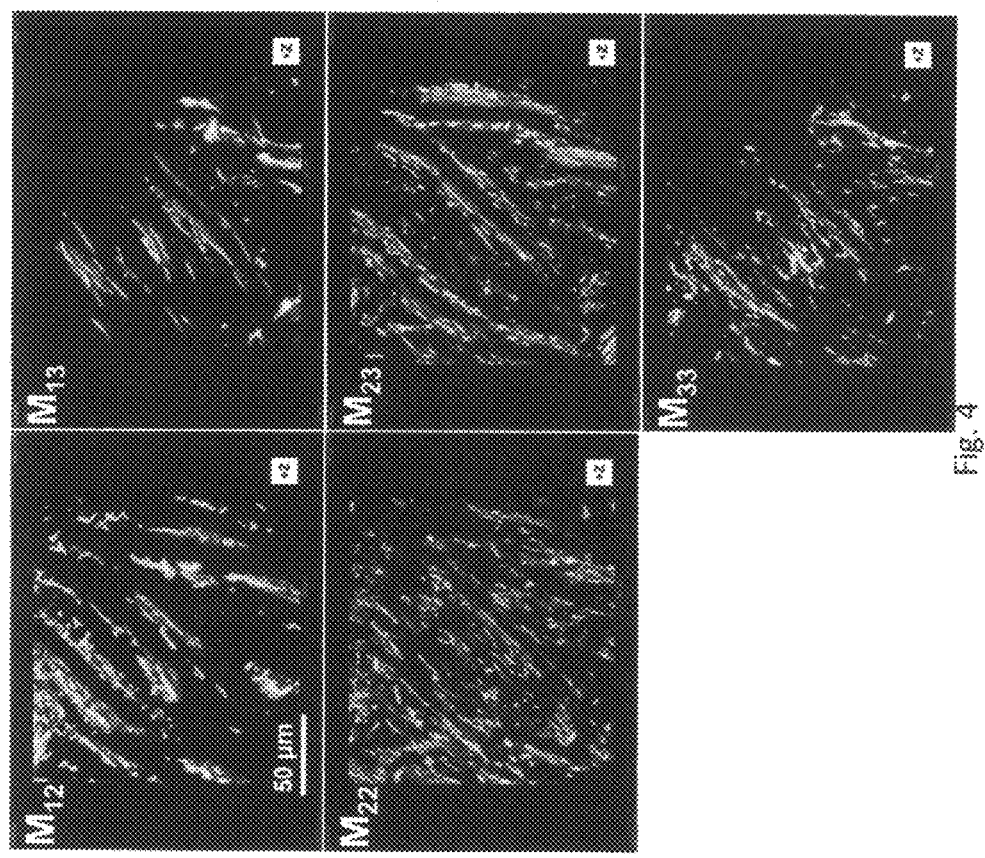
FIG. 4 shows 3-D Mueller Matrix volume rendering of combined focal slices for isolated Mueller Matrix values from +0.3 to +1.
Figure 5:
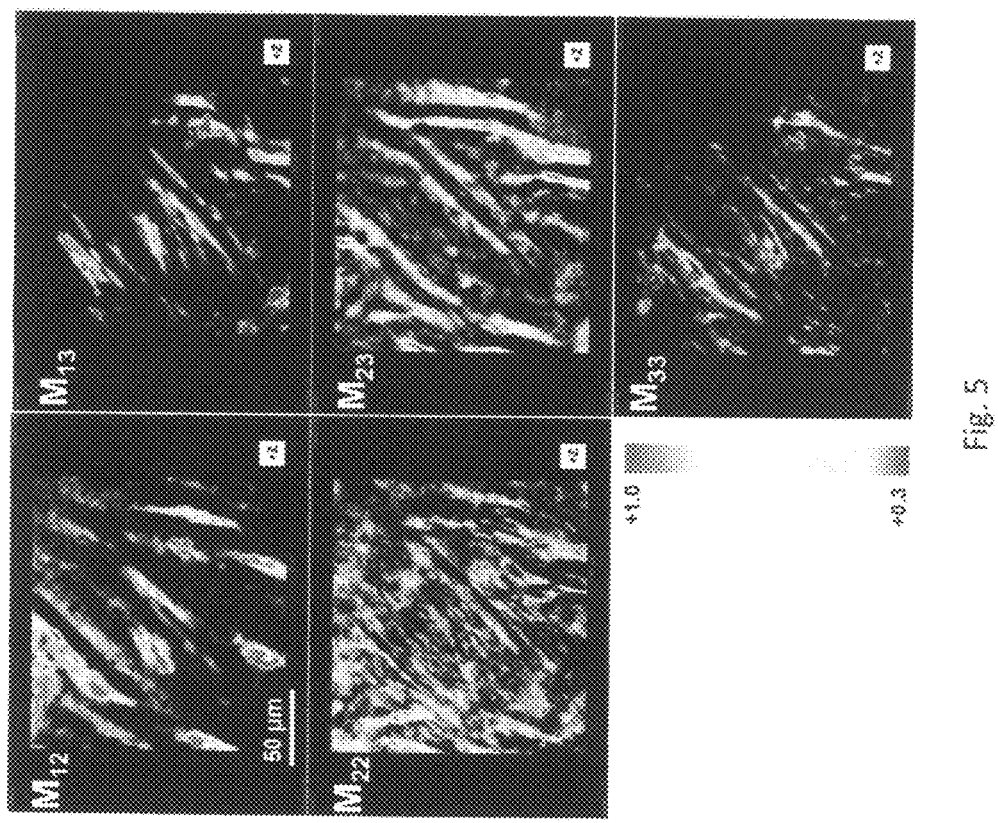
FIG. 5 shows 4-D Mueller Matrix volume rendering of combined focal slices for isolated Mueller Matrix values from +0.3 to +1.
Figure 6:
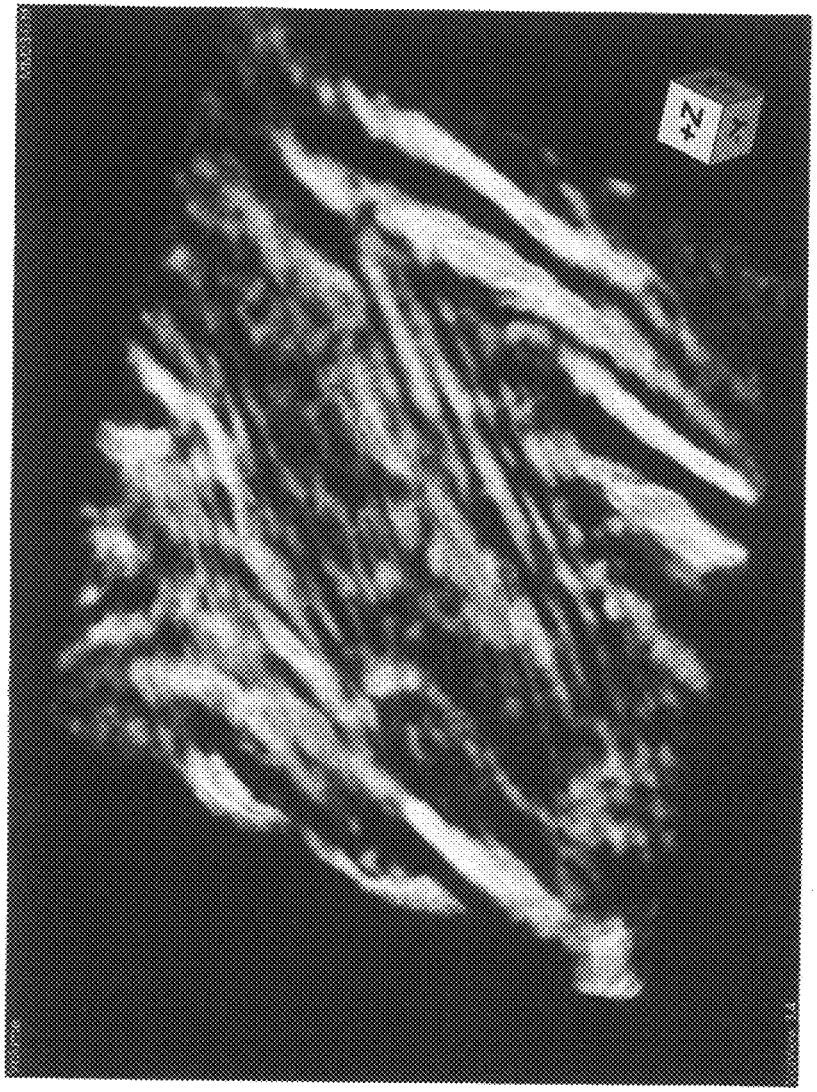
FIG. 6 shows a 4-D Mueller Matrix M23 Volume rendering.

Complimentary images of all ten focal slices for each MM element with isolated values were combined using VOL-View 3.4 software to obtain 3-D volume rendered images (see FIG. 4), and 4-D volume rendered images with corresponding MM intensity values per slice (see FIG. 5). Both 3-D and 4-D renderings demonstrate the isolation of cell structures that are suspect to facilitate interactions between the cells and the underlying nanostructured substrate. For example, the off-diagonal MM element M23 shows an external boundary of cells, which is suspected to be related to either the adhesive portion of the cell membrane as a whole or cellular adhesive components, such as integrins, which facilitate cell attachment to the nanostructured surface. Furthermore, the original MM element M22 appears to show less defined cellular features, but rather what is suspected to be isolation of the underlying nanostructure substrate, where MM values near +1 (indicated in FIG. 5), could indicate changes in birefringence caused by the cells interactions with the underlying nano-columnar surface, (eg. by means of column bending or cell attachment). FIG. 6 shows a 4-D Mueller Matrix Volume rendering of combined focal slices for isolated Mueller Matrix values from 0.3-+1 for Mueller Matrix Element M23 in a 3-D perspective rendering viewing at an oblique angle against cells on a birefringent support.

The present invention can be practiced with more conventional imaging approaches such as conformal microscopy with fluorescent labeling to corroborate the location of specific cell components, such as nuclei, focal adhesions, actin distribution, and cell Junction proteins, or to isolate cell components seen in corresponding MMBM studies. The present invention also lends itself to investigations of various cell lines, the effects of transmission vs. reflective ellipsometry and the use of various birefringent substrates, (eg. columns, spirals, helicies, flat surfaces, microstructured patterns), to demonstrate varying cell microenvironments as well as imaging configurations.

As alluded to before in this Specification, the present invention enables new imaging techniques to develop a non-labeling approach to evaluating phenotypic characteristics of cells, including cell and biomolecular interactions with nanostructured substrates. The images that application of the present invention produce will provide new information regarding cellular adhesive forces on nanostructured features, biomolecule internalization and release, and stem cell differentiation to aid in design of nanostructured cell-instructive biomaterial substrates.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A non-destructive method for producing magnified images of samples utilizing an anisotropic contrast technique in combination with use of sample investigating polarized electromagnetic radiation, said method comprising;
- a1) providing an optical system which produces magnified images of samples by an approach involving applying an investigating beam of electromagnetic radiation that has a polarization state imposed thereupon, thereto; and
- a2) providing at least one anisotropic transparent or semi-transparent element within the beam of electromagnetic radiation pathway, comprising a selection from the group consisting of:
    - one anisotropic transparent or semi-transparent region in an element within the beam of electromagnetic radiation pathway; and
    - more than one anisotropic transparent or semi-transparent region in an element within the beam of electromagnetic radiation pathway;

which at least one element is in proximity to the sample, which one or more anisotropic transparent or semi-transparent element(s) provide contrast in an image of said sample which is coupled therewith, based in changes of beam polarization state;

said method further comprising:
- b) providing a sample and causing it to interact with said at least one anisotropic transparent or semi-transparent element while said beam of electromagnetic radiation is caused to interact therewith;
- c) detecting images of electromagnetic radiation reflected from or transmitted through said sample, as a function of a change in polarization state of said beam of electromagnetic radiation caused by interaction with said sample and at least said anisotropic transparent or semi-transparent element;
- d) processing data pertaining to said detected images to provide at least some Jones or Mueller Matrix elements including at least one off-diagonal element thereof, that pertain to known "X", "Y" and "Z" locations of said sample;
- e) storing and/or displaying said processed data.

2. A non-destructive method as in claim 1, which further comprises analyzing detected image data to determine characterizing physical and/or chemical parameters of said sample.

3. A non-destructive method as in claim 1, in which the investigating beam of electromagnetic radiation is of a desired selectable wavelength in at least the THZ to VUV range and in which data is acquired at a selection from the group consisting of:
- a single wavelength; and
- multiple wavelengths.

4. A non-destructive method as in claim 1, in which detecting images of electromagnetic radiation reflected from or transmitted through said sample involves a light collecting system.

5. A non-destructive method as in claim 1, in which the step of providing an optical system comprises providing system capability to vary a position of said sample in "X" "Y" and "Z" directions.

6. A non-destructive method as in claim 1, in which the step of providing an optical system comprises providing system capability to vary a location on a sample from which light is collected, in three dimensions.

7. A non-destructive method as in claim 1, in which the step of providing an optical system comprises providing system capability that enables varying the sample magnification.

8. A non-destructive method as in claim 7, in which the system capability that enables varying the sample magnification is achieved by varying the beam path configuration.

9. A non-destructive method as in claim 1, in which the optical system further comprises an environmental chamber in which said sample is present.

10. A non-destructive method as in claim 9, in which the optical system's environmental chamber, in which said sample is present, is a fluid cell.

11. A non-destructive method as in claim 1, in which said one or more anisotropic transparent or semi-transparent element(s) demonstrate optically uniaxial or optically biaxial properties at a selected wavelength at which the optical system forms an image of said sample, and in which at least one of said optical axes is not oriented perpendicular to the surface of said element.

12. A non-destructive method as in claim 1, in which said one or more anisotropic transparent or semi-transparent element(s) demonstrate birefringence and/or dichroism at a selected wavelength at which the optical system forms an image of said sample.

13. A non-destructive method as in claim 1, in which said one or more anisotropic transparent or semi-transparent element(s) demonstrate one or two major axes of dichroic activity, and in which at least one of said axes is not oriented perpendicular to a surface of said element.

14. A non-destructive method as in claim 1, in which said one or more anisotropic transparent or semi-transparent element(s) demonstrate one or two major axes of dichroic activity as well as birefringence, and in which at least one of said axes is not oriented perpendicular to a surface of said element.

15. A non-destructive method as in claim 1, in which said one or more anisotropic transparent or semi-transparent element(s) comprised of porous material with regular arrangements of patterns and interspacings that have dimensions smaller than a selected wavelength at which an image of said sample is formed.

16. A non-destructive method as in claim 15, in which said one or more anisotropic transparent or semi-transparent element(s) are comprised of columnar nanostructured thin films.

17. A non-destructive method as in claim 16, in which said one or more anisotropic transparent or semi-transparent element(s) columnar nanostructured thin films are twisted chiral.

18. A non-destructive method as in claim 16 or 17, in which said one or more anisotropic transparent or semi-transparent element(s) columnar nanostructured thin films are formed by glancing angle deposition of micro or nano-fiber producing material.

19. A non-destructive method as in claim 1, in which said one or more anisotropic transparent or semi-transparent element(s) is comprised of both isotropic and anisotropic regions, and wherein said isotropic regions can serve as a support structure.

20. A non-destructive method as in claim 1, in which said one or more anisotropic transparent or semi-transparent element(s), in which the anisotropic region is comprised of at least one selection from the group consisting of:
- slanted columns;
- zig-zags;
- helices; and/or
- hollow screws.

21. A non-destructive method as in claim 1, in which the optical system comprises a polarization state generator and polarization state analyzer, each of which comprises a polarizer.

22. A non-destructive method as in claim 21 in which the optical system further comprises a compensator in at least one of said polarization state generator and polarization state analyzer.

23. A non-destructive method as in claim 21, in which a produced image of a sample is a function of both wavelength and beam polarization state.

24. A non-destructive method as in claim 1, in which each pixel in said stored or displayed processed data corresponding to produced Jones or Mueller matrix elements, including at least one off-diagonal element thereof, (J12, J21, M13, M14, M23, M24, M31, M32, M41 and M42), is calculated as a function of initial electromagnetic radiation beam polarization state and of the polarization state of said beam after interaction with said sample and at least one anisotropic transparent or semi-transparent element within the beam of electromagnetic radiation pathway to provide sample image data.

25. A non-destructive method as in claim 1, in which data is further collected for the case where no sample is present.

26. A non-destructive method as in claim 24, in which a comparison is made between data collected for specific "X", "Y" and "Z" positions on a sample when a sample is present and when it is not present and results thereof are stored or displayed.

27. A non-destructive method as in claim 24, in which data collected when a sample is not present, is subtracted from data collected at the same "X", "Y" and "Z" positions when it is present and results thereof are stored or displayed.

28. A non-destructive method as in claim 24, in which data collected for specific "X", "Y" and "Z" positions on a sample when a sample is present, is subtracted from data collected at different "X", "Y" and "Z" positions when it is present, and results thereof are stored or displayed.

29. A non-destructive method as in claim 24, in which data collected for specific "X", "Y" and "Z" positions on a sample when a sample is present, is subtracted from data collected at the same "X", "Y" and "Z" positions when it is still present, but where system components are varied in position, and results thereof are stored or displayed.

30. A non-destructive method as in claim 24 or 25 or 26 or 27 or 28 or 29, in which additional computation is performed to evaluate physical and/or chemical properties of said sample.

31. A non-destructive method for imaging at least one selection from the group of samples consisting of:
   biomolecules;
   biomaterial interfaces;
   cells;
   cell interactions;
   tissues; and
   tissue regeneration phenomena;
utilizing an anisotropic contrast technique in combination with use of sample investigating polarized electromagnetic radiation, said method comprising;
   a) providing a system capable of generating and imaging at least one element of a Jones or Mueller Matrix, said system comprising:
      a source of electromagnetic radiation;
      a polarization state generator;
      a stage for supporting samples, said stage comprising highly-ordered and micro to nano-scale structure architectures such that when a sample is placed thereupon and investigated with electromagnetic radiation, and an image is generated for said at least one element of a Jones or Mueller matrix, image information is shifted into off-diagonal elements thereof as a result of stage material anisotropy;
      a polarization state analyzer;
      a data detector for accepting electromagnetic radiation after it interacts with a sample placed onto said stage;
      a computer system for analyzing data provided by said data detector and producing imaging information for at least one element of a Jones or Mueller matrix; and
      a presentation screen for making Jones or Mueller matrix imaging viewable;
   b) placing a sample onto said stage;
   c) causing said source of electromagnetic radiation to direct a beam of electromagnetic radiation so that it passes through said polarization state generator, interacts with said sample and stage upon which it is present, passes through said polarization state analyzer and then enters said data detector;
to the end that sample characterizing data produced by said data detector is analyzed and presented for viewing as imaged Jones or Mueller matrix elements;
said method being characterized in that each pixel in stored or displayed processed data corresponding to produced Jones or Mueller matrix elements, including at least one off-diagonal element thereof, (J12, J21, M13, M14, M23, M24, M31, M32, M41 and M42), is calculated as a function of initial electromagnetic radiation beam polarization state and of the polarization state of said beam after interaction with said sample and at least one anisotropic transparent or semi-transparent element within the beam of electromagnetic radiation pathway to provide sample image data.

32. A non-destructive method as in claim 31, in which the provided system is further comprised of a focusing lens on one side of said stage for supporting samples, a collimating lens on another side of said stage for supporting samples such that magnification of images can be obtained.

33. A non-destructive method as in claim 31, wherein said computer system for analyzing data provided by said data detector and producing imaging information for at least one element of a Jones or Mueller matrix and said presentation screen for making Jones or Mueller matrix imaging viewable are embodied as a camera.

34. A non-destructive method as in claim 31, in which the electromagnetic beam interacts with said sample and stage upon which it is present such that it transmits therethrough.

35. A non-destructive method as in claim 31, in which the electromagnetic beam interacts with said sample and stage upon which it is present such that it reflects therethrough.

36. A non-destructive method as in claim 31, in which the stage for supporting samples is fabricated by glancing angle deposition of nano-fiber producing material onto a substrate.

37. A system which is system capable of generating and imaging at least one off-diagonal element of a Jones or Mueller matrix that is representative of a sample, said system comprising:
   a source of electromagnetic radiation;
   a polarization state generator;
   a stage for supporting samples;
   a polarization state analyzer;
   a data detector for accepting electromagnetic radiation after it interacts with a sample placed onto said stage;
   a computer system for analyzing data provided by said data detector and producing imaging information for at least one element of a Jones or Mueller matrix; and a presentation screen for making Jones or Mueller matrix imaging viewable;

said system being distinguished in that it comprises, between said polarization state generator and polarization state analyzer, a selection from the group consisting of:
- one anisotropic transparent or semi-transparent region in an element within the beam of electromagnetic radiation pathway; and
- more than one anisotropic transparent or semi-transparent region in an element within the beam of electromagnetic radiation pathway;

which at least one element is in proximity to the sample, which one or more anisotropic transparent or semi-transparent element(s) provide contrast in an image of said sample which is coupled therewith, based in changes of beam polarization state.

38. A system as in claim 37, in which the stage for supporting samples is fabricated by glancing angle deposition of nano-fiber producing material onto a substrate.

* * * * *